United States Patent [19]

Simon

[11] Patent Number: 5,167,780
[45] Date of Patent: Dec. 1, 1992

[54] PROCESS FOR THE DETERMINATION OF THE CONCENTRATION RATIO OF LITHIUM IONS TO SODIUM IONS COMPOSITION HAVING A HIGH SELECTIVITY FOR SODIUM IONS

[75] Inventor: Wilhelm Simon, Zurich, Switzerland

[73] Assignee: Willi Möller, Zurich, Switzerland

[21] Appl. No.: 102,192

[22] Filed: Sep. 29, 1987

[30] Foreign Application Priority Data

Jan. 10, 1986 [CH] Switzerland ................. 3927/86

[51] Int. Cl.[5] ............................................. G01N 27/46
[52] U.S. Cl. ............................ 204/153.1; 204/153.15
[58] Field of Search ............... 204/411, 412, 415, 416, 204/418, 419, 420, 1 T, 1 A, 153.1, 153.15; 357/25; 564/152, 160; 546/226

[56] References Cited

U.S. PATENT DOCUMENTS

| | | | |
|---|---|---|---|
| 4,269,682 | 5/1981 | Yano et al. | 204/418 |
| 4,409,088 | 10/1983 | Kanno et al. | 204/418 X |
| 4,452,682 | 6/1984 | Takata et al. | 204/416 X |
| 4,508,613 | 4/1985 | Busta et al. | 204/416 X |
| 4,512,870 | 4/1985 | Kohara et al. | 204/416 |
| 4,647,362 | 3/1987 | Watanabe | 204/411 |

OTHER PUBLICATIONS

Vatlina et al., "Synthesis . . . metals", Chem. Abstracts, vol. 88, 1978, 88:89174x.
Chemical Abstract 96:192451z (1982) abstracting Materova et al., Zh. Vses. Khim. O-va 27(1), 106-7 (1982).

*Primary Examiner*—Nam Nguyen
*Attorney, Agent, or Firm*—Seidel, Gonda, Lavorgna & Monaco

[57] ABSTRACT

The concentration ratio of lithium ions to sodium ions can be determined very accurately and excellently reproducible by using an electrode for the determination of lithium ions and an electrode for the determination of sodium ions and by contacting the ion sensitive members of said electrodes with the sample solution. The two electrodes are electrically connected via an instrument for the determination of the voltage and accordingly the potential difference $\Delta V$ between said two electrodes is determined. From said potential difference the concentration ratio of lithium ions to sodium ions in the sample solution can be calculated. It is furthermore possible to connect electrically the lithium electrode as well as the sodium electrode via an instrument for the determination of the voltage with a single external reference-electrode or a common-electrode and then from the two measured potential differences the potential difference $\Delta V$ between the lithium electrode and the sodium electrode is calculated.

4 Claims, 2 Drawing Sheets

PROCESS FOR THE DETERMINATION OF THE CONCENTRATION RATIO OF LITHIUM IONS TO SODIUM IONS COMPOSITION HAVING A HIGH SELECTIVITY FOR SODIUM IONS

BACKGROUND OF THE INVENTION

Very recently intensive investigations were made to provide lithium sensitive electrodes which have a sufficiently high selectivity for lithium ions over sodium ions so that they can be used for the determination of the concentration of lithium ions in such liquid media which contain far higher concentrations of sodium ions than of lithium ions, for instance per mol of lithium ions about one hundred mols of sodium ions. Such high requirements as to the selectivity of lithium over sodium have to be put if the lithium concentration is determined in biological fluids, like blood serum. Corresponding electrodes for the determination of the lithium concentration comprise a lithium selective membrane containing a lithium selective component which has to have a very high selectivity for lithium ions over sodium ions.

With those prior art lithium selective membranes which had the highest selectivity for lithium ions over sodium ions it was possible to determine lithium concentrations in aqueous media containing higher concentrations of sodium ions by using calibration curves which were calibrated with a fixed ion background. The molar lithium concentration in blood serum however is only about one hundredth of the molar sodium concentration in the blood serum and if accordingly the lithium concentration remains constant but the sodium concentration alters then the measured lithium concentration determined according to said fixed ion background calibration method also alters and the determined value of the lithium concentration accordingly is incorrect.

According to the present invention said problem can be avoided by determinating in the sample solution not the absolute lithium concentration or lithium activity but the concentration ratio of lithium ions to sodium ions. The present invention accordingly concerns a new process for the determination of the concentration ratio of lithium ions to sodium ions and an apparatus for performing said process.

DESCRIPTION OF THE PRIOR ART

Many dicarboxylic acid diamides which form with cations lipophilic complexes and which can be used as components of ion selective membranes for the determination of the concentration of the cations in question are already described in the prior art. Among said prior art dicarboxylic acid diamides there are to be found also such compounds which have a certain selectivity for lithium ions over other alkali metal ions.

The concentrations of the most important cations found in biological fluids, i.e. $Na^+$, $K^+$, $Ca^{2+}$ and $H^+$, can easily be determined in clinical laboratories using ion-selective electrodes equipped with a corresponding ion-selective membrane. Contrary to this, the assay of $Li^+$ is still performed in clinical laboratories by flame photometry or atomic absorption spectometry. The monitoring of the concentration of lithium ions in blood is very important during the lithium therapy of patients suffering from manic-depressive psychosis and if lithium is administered in order to prevent such manic-depressive psychosis. With regard to this there is referred to the publications of A. Amdisen and M. Schou in "Münch. Med. Wochenschr.", 117(1975) 1417 and A. Amdisen, in Dan. Med. Bull., 22(1975) 277.

In clinical tests usually concentrations of lithium ions have to be measured which are in the range of 0.7 mmol to 1.5 mmol, and said determination has to be performed in the presence of far higher concentrations of sodium ions, like e.g. concentrations in the range of 135 mmol to 150 mmol. This is e.g. true if the concentration of lithium ions has to be determined in blood serum or whole blood.

In the European patent publication no. 0 174 572 two specific cyclohexane-1,2-dicarboxylic acid diamides are described and said two prior art compounds are those which had the highest selectivity for lithium ions over the alkali metal ions found until then. Said cyclohexane-1,2-dicarboxylic acid diamides have the formula I

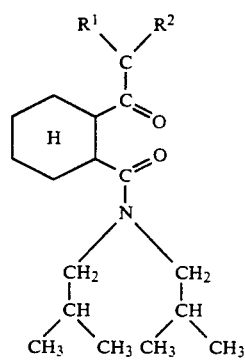

wherein the group of formula

has either the structure

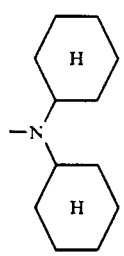

or the structure

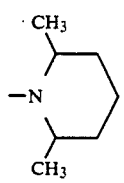

Ion selective membranes which contain as ion selective component one of the two cyclohexane-1,2-dicarboxylic acid diamides described in said European patent publication no. 0 174 572 and furthermore o-nitrophenyl-n-octylether as plasticizer have a high selectivity for lithium ions over sodium ions but the corresponding value of $$\log K_{LiNa}^{Pot}$$

still does not completely fulfil the requirements which have been put, if the concentration of the lithium ions has to be determined in blood serum which about has a hundredfold concentration of interfering sodium ions. According to the Nicolskii-Eisenman equation a value of $$\log K_{LiNa}^{Pot}$$

of 4,3 would be desirable. The clinical range of lithium concentrations however is only slightly above the level at which the lithium ions can be detected with ion selective membranes containing said compound of formula I as lithium selective component. Accordingly a determination of the concentration of the lithium ions with ion selective membranes containing said prior art compounds of formula I is only possible, if a fixed ion background calibration is used.

Even if said calibration with fixed ion background is made, however there remain uncertainties in the electromotive force (EMF) determined with electrodes, the lithium ion sensitive membranes of which contain as ion selective component one of the compounds of formula I. Said uncertainties are for the best membranes in the range of 0.74 millivolt. Said variations in the determined EMF are due to the varying concentrations of sodium ions encountered in the tested blood samples. The concentrations of sodium ions in serum samples are in the range of 135-150 mmol, and accordingly the ion background of serum samples is actually not fixed but variable within the stated range. This results in uncertainties in the determined lithium concentration of about 5.1% for the best membranes tested.

A further disadvantage of the best until now known membranes for the determination of lithium ions, which contain as ion selective component a cyclohexane-1,2-dicarboxylic acid diamide of formula I and furthermore the o-nitrophenyl-n-octylether as plasticizer, is, that said membranes have only a rather short period of life (only a few weeks) if they are frequently contacted with blood serum or whole blood.

The publication Analytical Chemistry, vol. 50, number 6, May 1978, pages 811-817, concerns the determination of a specific ion in the presence of interfering ions, which interfering ions optionally are present in the sample solution in far high concentrations than the ion, the concentration of which has to be determinated. Corresponding test results for the determination of sodium ions in the presence of varying concentrations of potassium ions, optionally far higher concentrations of potassium ions, are stated. Corresponding apparatus which comprise a sodium selective electrode and potassium selective electrode and a common reference-electrode, are described in FIG. 1 and 2 and it is explained that when the null-point potentiometry was used differential measurements between two ion selective electrodes of the same kind, like two ion selective sodium electrodes, were made.

It can be seen from the equation 3 on page 815, left column, that with said measurements the activity of a specific ion i was determined in the presence of the interfering ion j, that however not the concentration ratio of the ion i to the ion j was measured. Also the corresponding tables III and IV on page 816 show that always the concentration of sodium ions in the presence of potassium ions respectively the concentration of potassium ions in the presence of sodium ions was determined (see column 2, respectively 5 of said tables where the found values are compared with the actual values of the corresponding test solutions). In column 3 of tables III and IV, furthermore, also a potassium to sodium ratio is stated. Said ratio however is the corresponding taken ratio of the test solution and not the measured value.

SUMMARY OF THE INVENTION

It was the aim of the present invention to avoid difficulties which occur when the concentration of lithium ions has to be determined in the presence of a higher and not constant but variable concentration of sodium ions. It was found out that said aims can be achieved by measuring instead of the concentration of the lithium ions the corresponding concentration ratio of lithium ions to sodium ions. Accordingly the apparatus for performing said new process comprises in addition to an ion sensitive electrode for the determination of lithium ions also an ion sensitive electrode for the determination of sodium ions and the measurement is performed so that the concentration ratio of lithium ions to sodium ions is determinated.

When in test solutions a predetermined low and constant concentration of lithium ions is present and furthermore a far higher and variable concentration of sodium ions then the lithium activities measured with a lithium sensitive electrode, according to the prior art processes varies due to the different sodium concentrations in the tested sample solutions. Said deficiency is avoided with the inventive process according to which not the concentration respectively activity of the lithium ions is determinated but the concentration ratio of lithium ions to sodium ions.

DETAILED DESCRIPTION OF THE INVENTION

Figure 1:
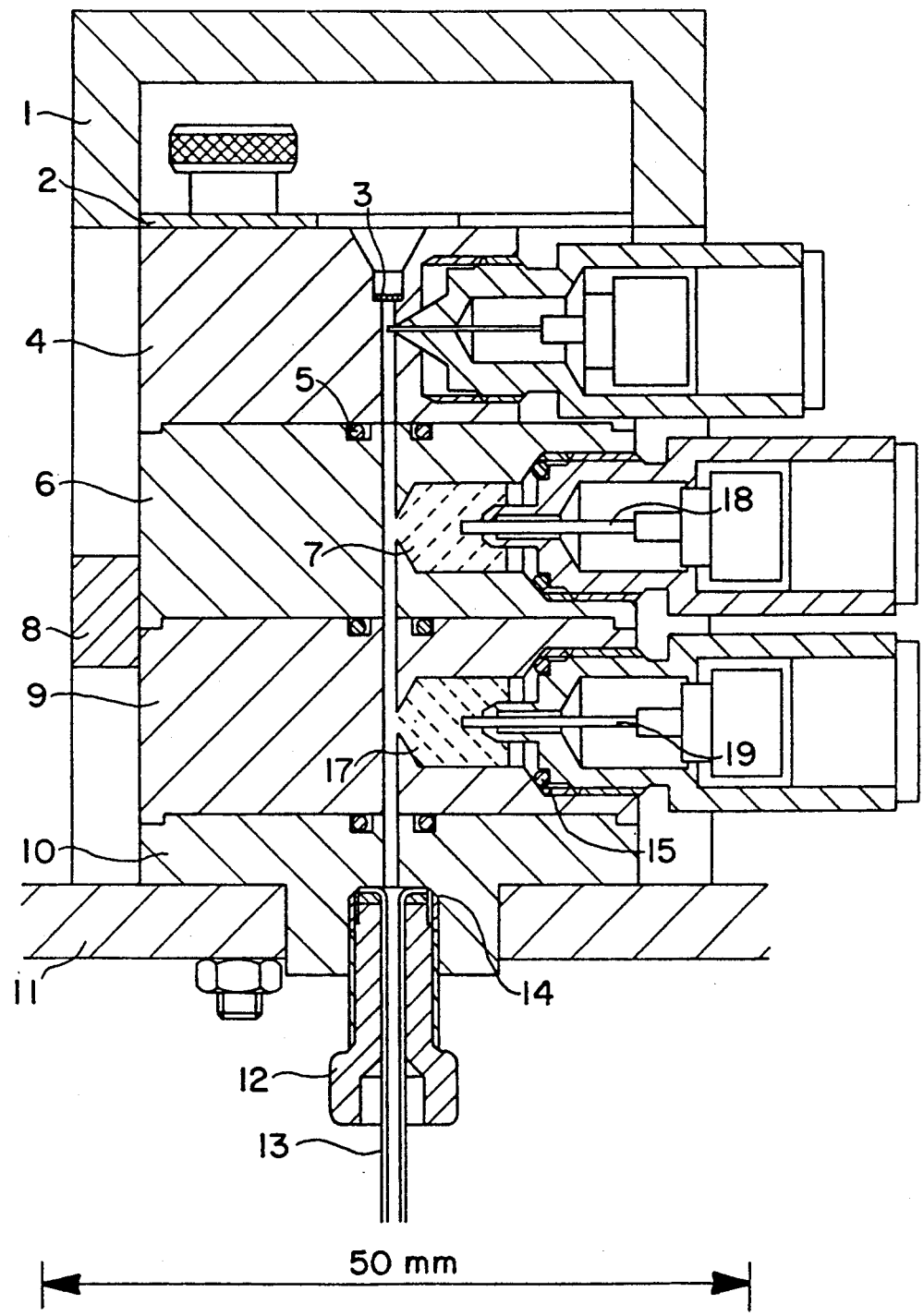
FIG. 1 is a schematic cross-sectional view of a flow-through electrode system according to the invention, for determining the concentration ratio of lithium ions to sodium ions.

One object of the present invention accordingly is a process for the determination of the concentration ratio of lithium ions to sodium ions in a sample solution. Said process is characterized in that the sample solution is either.

A) brought into contact with an electrode for the determination of lithium ions and an electrode for the determination of sodium ions and the potential difference $\Delta V$ between said two electrodes is measured or B) the sample solution is contacted with an electrode for the determination of lithium ions and an electrode for the determination of sodium ions and that, furthermore a single external reference-electrode or a common-electrode is used, and that the potential difference $V_1$ between the lithium electrode and the reference-electrode or the common-electrode, and the potential difference $V_2$ between the sodium electrode and the reference-electrode or the common-electrode is measured and wherein the value of $V_1-V_2$ corresponds to the potential difference $\Delta V$ between the lithium electode and the sodium electrode and that from the potential difference $\Delta V$ the concentration ratio of lithium ions to sodium ions is calculated.

The inventive process is specially advantageous when the concentration ratio of lithium ions to sodium ions is determined in a sample solution in which the concentration of sodium ions is far higher than the concentration of lithium ions, for example a sample solution in which the molar ratio of lithium ions to sodium ions is 1:100.

If the ion sensitive membrane of an ion sensitive electrode for the determination of lithium ions and an external reference-electrode and optionally a common-electrode is immersed into a sample solution and if a fixed ion background calibration is used for said sensor cell assembly and the lithium ions are determined in sample solutions using a corresponding calibration curve based on the fixed ion background calibration then the activities of lithium ions are measured in accordance with the Nikolskii-Eisenman equation. If in this system a series of sample solutions is measured in which the lithium concentration is kept constant, however the ion background differs from sample to sample then the measured activity of the lithium ions also differs from sample to sample due to the different ion background.

In biological systems like e.g. in the blood serum the molar amount of sodium ions is about a hundredfold of the molar amount of lithium ions and furthermore the molar amount of sodium ions in said blood serum is not constant but varies within a rather broad range. Said variations of the ion background, e.g. variations of the concentrations of the sodium ions, result in corresponding alternations of the activity coefficient of each single species of ions and accordingly in an alternation of the activity coefficient of lithium ions as well as in an alternation of the activity coefficient of the sodium ions. Assuming that the activity coefficient of the sodium ions and the activity coefficient of the lithium ions is submitted to an about similar alternation or variation when the ion background of the sample solution varies and if the potential difference $\Delta V$ between the electrode for the determination of the lithium ions and the electrode for the determination of the sodium ions is measured, said alterantions of the activity coefficient of the lithium ions and the activity coefficient of the sodium ions are balanced or nearly compensated so that actually in said sample solutions the concentration ratio of lithium ions to sodium ions is determined. Accordingly the above stated uncertainties in the measured lithium concentration due to a variation of the activity coefficient of the lithium ions because of a variation of the ion background are avoided if not the concentration of the lithium ions but the concentration ratio of lithium ions to sodium ions is determinated. It furthermore was found out that the concentration of sodium ions, i.e. the sodium level, in the blood serum varies in a rather broad range from human being to human being. It is usually assumed that the physiological range of the sodium ions in the blood serum is 135 mmol to 150 mmol of sodium ions, but if corresponding tests are performed with human beings then some of them have sodium concentrations in the blood serum which are very near to or even below the above stated lower limit while other human beings have in the blood serum sodium concentrations which are near to or even above the stated upper limit. If a person who suffers from manic depressive psychosis is submitted to a therapeutical administration of lithium ions then it was found out that those persons who have a high sodium content in their blood serum tolerate a too high dosis of lithium ions far better than persons who have low content of sodium ions in their blood serum. Accordingly in the clinical application the determination of the concentration ratio of lithium ions to sodium ions is far more important than the determination of the concentration of lithium ions without drawing into consideration also the sodium level in the blood serum of the persons in question.

According to a preferred embodiment of the claimed process therefore the concentration ratio of lithium ions to sodium ions is determinated in sample solutions in which the lithium concentrations are in the range of 0.7–1.5 mmol, and the sodium concentrations are in the range of 135–150 mmol.

According to a more preferred embodiment of the invention the inventive process concerns the determination of the concentration ratio of lithium ions to sodium ions in body fluids, preferably in whole blood, blood serum or blood plasma.

A further object of the present invention is an apparatus for the performance of the inventive process, which apparatus comprises:

A) an electrode for the determination of lithium ions
B) an electrode for the determination of sodium ions and wherein
either the lithium sensitive electrode is electrically connected with the sodium sensitive electrode via an instrument for the determination of the voltage or the apparatus comprises in addition to the lithium selective electrode and the sodium selective electrode furthermore a common external reference-electrode or a common-electrode and wherein the lithium selective electrode is electrically connected with the external reference-electrode or the common-electrode via an instrument for the determination of the voltage and wherein, furthermore, the sodium selective electrode is electrically connected with the same external reference-electrode or common-electrode via an instrument for the determination of the voltage, and wherein during the performance of the determination of the concentration ratio of lithium ions to sodium ions the ion sensitive member of the lithium electrode and the ion sensitive member of the sodium electrode is contacted with the sample solution, and the optionally present external reference-electrode or the optionally present common-electrode is either contacted with the sample solution or not contacted with the sample solution.

In said apparatus the electrode for the determination of the activity of lithium ions and also the electrode for the determination of the activity of sodium ions can e.g. be a corresponding ion sensitive electrode which comprises an internal filling solution into which the internal reference-electrode extends and furthermore an ion selective membrane which contains the ion selective component for the ion to be determinated, i.e. either a lithium selective component or a sodium selective component, and said ion selective membrane contacts with its inner surface the internal filling solution of the electrode and with its outer surface the sample solution, when said sample solution is measured.

Such a preferred apparatus for the determination of the concentration ratio of lithium ions to sodium ions comprises:

A) an electrode for the determination of the activity of lithium ions, which lithium selective electrode comprises an internal filling solution into which the internal reference-electrode extends, and a lithium selective membrane which contains a lithium selective component, B) an electrode for the determination of the activity of sodium ions, which sodium selective electrode comprises an internal filling solution into which the internal reference-electrode extends, and a sodium selective membrane which contains a component which is selective for sodium ions, and either the internal reference-electrode of the lithium sensitive electrode is connected electrically with the internal reference-electrode of the sodium sensitive electrode via an instrument for the determination of the voltage, or the apparatus comprises in addition to the lithium selective electrode and the sodium selective electrode furthermore a common external reference-electrode or a common-electrode and wherein the internal reference-electrode of the lithium selective electrode is electrically connected with the external reference-electrode or the common-electrode via an instrument for the determination of the voltage and also the internal reference-electrode of the sodium selective electrode is electrically connected with the same external reference-electrode or common-electrode via an instrument for the determination of the voltage and that the ion sensitive membrane of the lithium electrode and the ion sensitive membrane of the sodium electrode is contacted with the sample solution during the performance of the determination of the concentration ratio and the optionally present external reference-electrode or optionally present common-electrode is either contacted with the sample solution or not contacted with the sample solution.

So called common-electrodes, like e.g. a platin wire immersed into the sample solution are used since several years for the determination of the potential difference, i.e. the electromotive force, of cell assemblies in addition to the external reference-electrode which is equipped with a liquid junction. Thus advantages can be achieved in the technique of performing the measurements and it is also possible to use such a common-electrode instead of an external reference-electrode. Further details concerning such common-electrodes are explained in the publication of P. Anker, E. Wieland, D. Ammann, R. E. Dohner, R. Asper and W. Simon "Neutral Carrier Based Ion Selective Electrode for the Determination of Total Calcium in Blood Serum" in Analytical Chemistry, 1981, 54, 1970, pages 1970–1974, and in said publication also a flow-through cell assembly equipped with such a common-electrode is illustrated schematically.

The inner filling solution of the electrode for the determination of lithium ions contains lithium chloride and the internal reference-electrode of said lithium electrode was a silver wire coated with silver chloride. The inner filling solution of the electrode for the determination of sodium ions contains sodium chloride and the internal reference-electrode of said sodium sensitive electrode was as well a silver wire coated with silver chloride.

The determinations accordingly were performed with the following type of cell assembly:

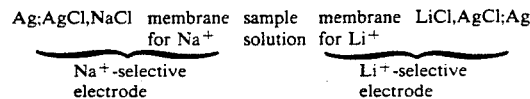

The electromotive force, i.e. the EMF, was determined for the above stated cell assembly and it was stated in millivolt. Based on the Nicolskii-Eisenmann equation (JUPAC) for the lithium selective half cell and the sodium selective half cell, respectively, the EMF of the above stated cell assembly corresponds to the following formula:

$$EMF[mV] = E_o + s \cdot \log\left(\frac{a_{Li}}{a_{Na}} + K_{LiNa}^{Pot}\right)$$

In said formula the symbols have the following meaning:

$E_o$ is the constant EMF difference which is dependent from the temperature, $s = 2.303\, RT/F = 59.16$ mV (at 25° C.), $K_{LiNa}^{Pot}$ = selectivity factor for the lithium selective electrode, $a_{Li}$ = activity of the lithium ions in the sample solution, $a_{Na}$ = activity of the sodium ions in the sample solution.

For the above stated equation the following was assumed:

1. The half cell which is selective for the lithium ions and furthermore also the half cell which is selective for the sodium ions have in pure salt solutions which contain only lithium salts and only sodium salts respectively, the theoretical Nernstian response.

2. The sodium selective electrode shows no interference by other ions which are present in the sample solution.

3. The lithium selective electrode is exhibiting only interference by the sodium ions present in the sample solution, it however shows no interference by other ions present in the sample solution.

Assuming further equal single ion activity coefficients for the lithium ions and the sodium ions then the EMF for the above stated cell assembly can be described by using instead of the formula stated before the following formula:

$$EMF[mV] = E_o + s \cdot \log\left(\frac{c_{Li}}{c_{Na}} + K_{LiNa}^{Pot}\right).$$

In the above stated formula the symbols have the following meaning:

$c_{Li}$ = the molar concentration of lithium ions in the sample solution $c_{Na}$ = the molar concentration of sodium ions in the sample solution.

The meaning of the remaining symbols was already explained in connection with the first equation stated before.

According to a preferred embodiment of the inventive apparatus said apparatus is a flow-through electrode system which comprises a thin channel, which is suited for the introduction of the sample solution and wherein into said channel there extends the ion selective membrane of the lithium selective electrode, the ion selective membrane of the sodium selective electrode and optionally furthermore the external reference-electrode, respectively eventually also the common-electrode.

When the apparatus is used for the determination of the concentration ratio of lithium ions to sodium ions, then the sample solution contacts the membrane of the lithium selective electrode as well as the membrane of the sodium selective electrode. As already explained, optionally an external reference-electrode is present and usually it is advantageous if said external reference-electrode also extends into the channel into which the sample solution is introduced so that it as well is in contact with the sample solution when the ratio of the ion concentration is determinated.

Provided that the apparatus comprises a common-electrode then said common-electrode either extends into said channel or it does not extend into the channel into which a sample solution is introduced.

Flow-through electrode systems can be used for the determination of small volumes of samples like samples having a volume of about 15 μl. A specific embodiment of such a flow-through electrode is described in detail in example 2 and it is furthermore also illustrated schematically in FIG. 1.

In the inventive apparatus the ion sensitive membrane of the electrode for the determination of lithium ions contains a component sensitive for lithium ions and preferably furthermore a polymer matrix, for example a polymer matrix of poly(vinylchloride). Usually said membranes contain as further component a plasticizer, preferably a rather nonpolar lipophilic plasticizer.

Also the electrode for the determination of the sodium ions comprises a membrane which is sensitive for sodium ions which contains a component selective for said sodium ions. Preferably the membrane furthermore comprises a polymer matrix, for instance a corresponding matrix of poly(vinylchloride). Optionally the sodium sensitive membrane comprises as further component a plasticizer, preferably a rather nonpolar lipophilic plasticizer.

Preferred lithium selective components of the electrode for the determination of lithium ions are the two prior art cyclohexane-1,2-dicarboxylic acid diamides described in the European patent publication 0 174 572, which compounds correspond to the following formula I

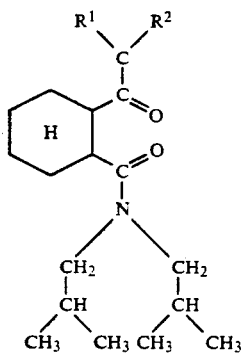

In said formula I the group of formula

has either the structure

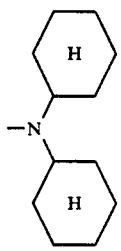

or the structure

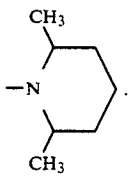

Of said two compounds of formula I the one is preferred in which the amide forming amine is dicyclohexylamine, i.e. the first named compound is preferred over the second named compound.

Further preferred lithium selective components of the membranes of the lithium electrodes used for performing the inventive process are the new dicarboxylic acid diamides of formula II

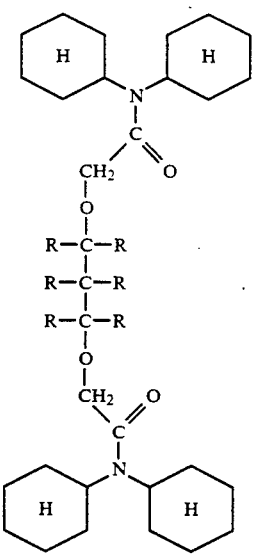

In said formula II the radicals R are selected from the group comprising hydrogen atoms, alkyl groups having 1-20 carbon atoms, alkenyl groups having 2-20 carbon atoms and alkynyl groups having 2-20 carbon atoms. The lithium selective components of formula II are described in the USA patent (patent application Ser. No. 099,579 filed Sep. 22, 1987 of the applicant for which the priority of the Swiss patent application 3795/86-6 of Sep. 23, 1986, is claimed.

The electrode for the determination of the sodium ions can contain in its sodium selective membrane any of the prior art substances which have a selectivity for sodium ions. Said membrane however can also contain a new sodium selective component which until now had not yet been described.

Preferred sodium selective components are the dicarboxylic acid diamides. Of said dicarboxylic acid diamides those are specially preferred, in which each of the two carboxamide groups of said dicarboxylic acid diamide is bonded to a saturated or unsaturated aliphatic residue, a cycloaliphatic residue or an aromatic residue through an aliphatic chain having 1-4 members of said chain and which aliphatic chain is a hydrocarbon chain or a hydrocarbon chain which is interrupted by an ether oxygen atom.

Specially preferred such sodium selective components which are contained in the membranes of the sodium selective electrode, are new dicarboxylic acid diamides having the following formula III

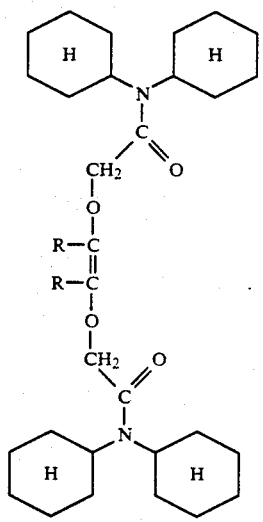

III

In said formula III the radicals R are either selected from the group comprising hydrogen atoms, alkyl groups having 1-20 carbon atoms, alkenyl groups having 2-20 carbon atoms and alkynyl groups having 2-20 carbon atoms or in said formula III the two radicals R form together with the carbon atoms to which they are bonded, a cycloaliphatic residue or aromatic residue.

The last mentioned compounds of formula III are the more preferred sodium selective compounds and of said group those compounds are specially preferred in which the group having the structure

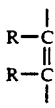

is an aromatic residue of formula

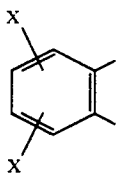

in which the two substituents

X are either selected from the group comprising hydrogen atoms, comparatively unpolar substituents like alkyl groups, alkenyl groups, aryl groups, nitro groups or halide atoms, or the two groups X form together with the carbon atoms to which they are bonded, a condensed aromatic nucleus or condensed heteroaromatic nucleus.

A specific example of a sodium selective component of said preferred class is the N,N,N',N'-tetracyclohexyl-1,2-phenylene-dioxydiacetamide, i.e. the corresponding compound in which in the aromatic residue of the stated formula of groups X are hydrogen atoms.

A further object of the present invention are the new sodium selective components having the above stated formula III, wherein the radicals R are as defined above and furthermore the preferred embodiments of said new sodium selective components of formula III defined above.

The following not limitative examples will illustrate electrodes for the determination of lithium ions and electrodes for the determination of sodium ions which can be used for performing the inventive processes, as well as the performance of the inventive process and furthermore a specific embodiment of an inventive apparatus, i.e. a flow-through electrode system for the determination of the concentration ratio of lithium ions to sodium ions.

EXAMPLE 1

Preparation of Ion Sensitive Membranes for Electrodes for the Determination of Lithium Ions and Electrodes for the Determination of Sodium Ions Preparation of the Membrane 1 and the Membrane 2

The membrane 1 and the membrane 2 is a membrane for the determination of lithium ions and each of said two membranes contains as ion selective component prior art compounds of formula I described in the European patent publication 0 174 572, in which the radical $R^1$ and also the radical $R^2$ is a cyclohexyl radical.

The membrane 1 and also the membrane 2 contain 2.6% by weight, referred to the total weight of the membrane, of said ion sensitive component and furthermore 32.3% by weight, referred to the total weight of the membrane of poly(vinylchloride).

The membrane 1 and the membrane 2 however contain different plasticizers.

The membrane 1 contained 64.7% by weight, referred to the total weight of the membrane, of the plasticizer o-nitrophenyl-n-octylether and furthermore 0.4% by weight, referred to the total weight of the membrane of the additive potassium-tetrakis (p-chloro-phenyl)borate.

The membrane 2 contained as plasticizer 64.5% by weight, referred to the total weight of the membrane of the ester-plasticizer having the following formula IV

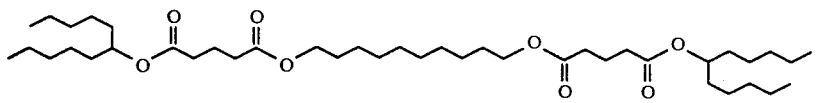

IV and furthermore 0.6% by weight, referred to the total weight of the membrane of the additive potassium-tetrakis(p-chloro-phenyl)borate.

Membrane 3

The membrane 3 is also a lithium selective membrane. It contained 2.0% by weight, referred to the total weight of the membrane of a new lithium selective component according to formula II stated before. Said new lithium selective component of the generic formula II had the following structure

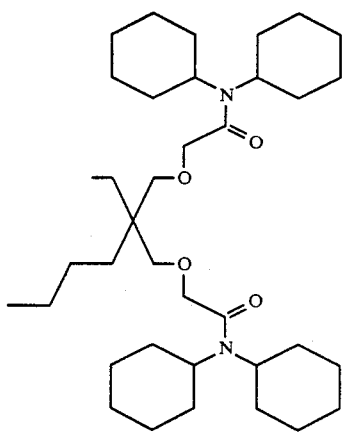

Said membrane 3 contained furthermore 32.4% by weight, referred to the total weight of the membrane, of poly(vinylchloride) and 65.6% by weight, referred to the total weight of the membrane, of a plasticizer which is a dicarboxylic acid diester. Said ester-plasticizer was the diester of adipic acid with the esterifying alcohol component nonane-5-ol.

Membrane 4

Said membrane was a sodium selective membrane. The membrane 4 contained as ion selective component the new compound of formula III stated before in which the group of formula

is an aromatic residue of formula

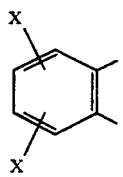

in which both groups X are hydrogen atoms.

The membrane 4 contained 1.0% by weight, referred to the total weight of the membrane, of said sodium sensitive component and furthermore 33% by weight, referred to the total weight of the membrane, of poly(vinylchloride) and 66% by weight, referred to the total weight of the membrane, of a plasticizer. The used plasticizer was the ester plasticizer of formula IV, which was already described with regard to the preparation of the lithium sensitive membranes 1 and 2.

EXAMPLE 2

Flow-Through Electrode System for the Determination of the Concentration Ratio of Lithium Ions to Sodium Ions FIG. 1 is a schematic cross-sectional view of said flow-through electrode.

The sample solution is introduced into the channel (13). The sample solution contacts the ion sensitive membrane of the sodium sensitive electrode (17) and also the ion sensitive membrane of the lithium electrode (7). Furthermore in the specific embodiment illustrated in FIG. 1 also the common-electrode, i.e. a platin wire, extends into said channel (13).

The top of the flow-through channel (13) is equipped with a network (3) of platin. The apparatus is mounted on a bottom plate (11) and the lid (1) covers said equipment. The flow-through channel extends through the ground-plate (14) and the ring (5).

The electrode for the determination of sodium ions (17) was equipped with a ring (15) and also the electrode for the determination of the lithium ions (7) was equipped with such a ring.

The internal filling solution of the sodium selective electrode (17) contacts the ion selective membrane of said electrode and the region where said internal filling solution is present is illustrated in the drawing by a shading with interrupted lines. In an analogous way the internal filling solution of the lithium selective electrode (7) also contacts the lithium selective membrane of said lithium selective electrode and also here the region which is filled with the internal filling solution is demonstrated in the drawing with a shading in which the lines are interrupted. It can be seen from said drawing that the inner side of the ion selective membrane of the ion selective electrode (17) is in contact with the internal filling solution of said electrode, while the outer side of the ion selective membrane of said electrode is in contact with the sample solution which had been introduced into the channel (13). The same is also true for the lithium selective electrode (7).

The sample solution is introduced from the top of said apparatus through the platin-network (3) and it flows through the channel (13) and finally into a tube of plastic material which extends through the screw of plastic material (12).

The screening or shielding (8), the bottom plate (11) and the lid (1) of said apparatus are made of metal, for example of aluminum.

In said flow-through electrode system the lithium selective membranes 1, 2 and 3 described in example 1 were tested in combination with the sodium selective membrane 4 described in example 1.

The internal reference-electrode (19) of the electrode for the determination of sodium ions (17) is connected electrically with the common-electrode via an instrument for the determination of the voltage, which instrument is not shown in FIG. 1. The internal reference-electrode (18) of the electrode for the determination of the lithium ions (7) is as well electrically connected with the common-electrode via an instrument for the determination of the voltage, which is not shown in FIG. 1.

EXAMPLE 3

Electrodes for the Determination of Lithium Ions Respectively Sodium Ions Which Are Coated Wire Electrodes The ion selective components of the membranes 1 and 3 of example 1 in a matrix of poly(vinylchloride) was applied to a silver wire which had been coated with silver chloride. Thus a so called coated wire electrode for the determination of lithium ions was prepared. Optionally the poly(vinylchloride) matrix containing the ion selective component furthermore contained a plasticizer.

According to the above described process the ion selective component of the membrane 4 of example 1 was applied in a matrix of poly(vinylchloride) onto a silver wire which prior had been coated with silver chloride. The corresponding electrode was a coated wire electrode which has a selectivity for sodium ions. Optionally the matrix of poly(vinylchloride) contained as further component a plasticizer.

The lithium selective coated wire electrode which contained the ion selective component of membrane 1 of example 1 was immersed in a sample solution and the sodium selective coated wire electrode was as well immersed into said sample solution. The two electrodes were electrically connected with each other via an instrument for the determination of the voltage.

A similar apparatus for the determination of the concentration ratio of lithium ions to sodium ions was made, however in this case the lithium selective electrode was the coated wire electrode which contained as ion selective component the corresponding compound of membrane 3 of example 1.

With said equipment the concentration ratio of lithium ions to sodium ions could be determinated in the sample solution and the results were very accurate and reproducible. In a further test the coated wire electrodes were electrically connected via a common-electrode and in said test the reproducibility of the test results was sometimes still better.

EXAMPLE 4

Planar Electrode System for the Determination of the Concentration Ratio of Lithium Ions to Sodium Ions In the same way as described in example 3 the ion sensitive components of the membranes 1 and 3 of example 1 and the ion sensitive component of the membrane 4 of example 1 was used for preparing according to the planar technique a sensor for the determination of the concentration ratio of lithium ions to sodium ions.

Onto discrete regions of the surface of a planar electrically conductive web or tape of silver/silver chloride there was applied the sodium selective component of the membrane 4 of example 1 and the lithium selective component of the membrane 1 of example 1 respectively. In an other test the lithium selective region of said planar semiconductor device comprised the lithium selective component of membrane 3 of example 1. The so prepared planar sensors are ion selective field-transistors and with said system a very accurate determination of the concentration ratio of lithium ions to sodium ions in a sample solution was possible and furthermore the reproducibility of the determined values was excellent.

EXAMPLE 5

Determination of the Concentration Ratio of Lithium Ions to Sodium Ions Using a Flow-Through Electrode System The lithium selective membranes 1, 2 and 3 of example 1 were tested, each in combination with the sodium selective membrane 4 of example 1 using the flow-through electrode described in example 2.

The sample solutions in which the concentration ratio of lithium ions to sodium ions was determined according to the inventive process were aqueous solutions as well as blood serum. The tests showed that in said sample solutions the determined concentration ratio was very accurate and furthermore very well reproducible. This shows that the assumptions which were made with regard to the interference of the sodium selective electrode and the lithium selective electrode by other ions are correct and that accordingly the concentration ratio of lithium ions to sodium ions of the sample solutions can be calculated according to the corresponding formula $$EMF[mV] = E_o + s \cdot \log \left( \frac{c_{Li}}{c_{Na}} + K_{LiNa}^{Pot} \right)$$

as already explained before.

Figure 2:
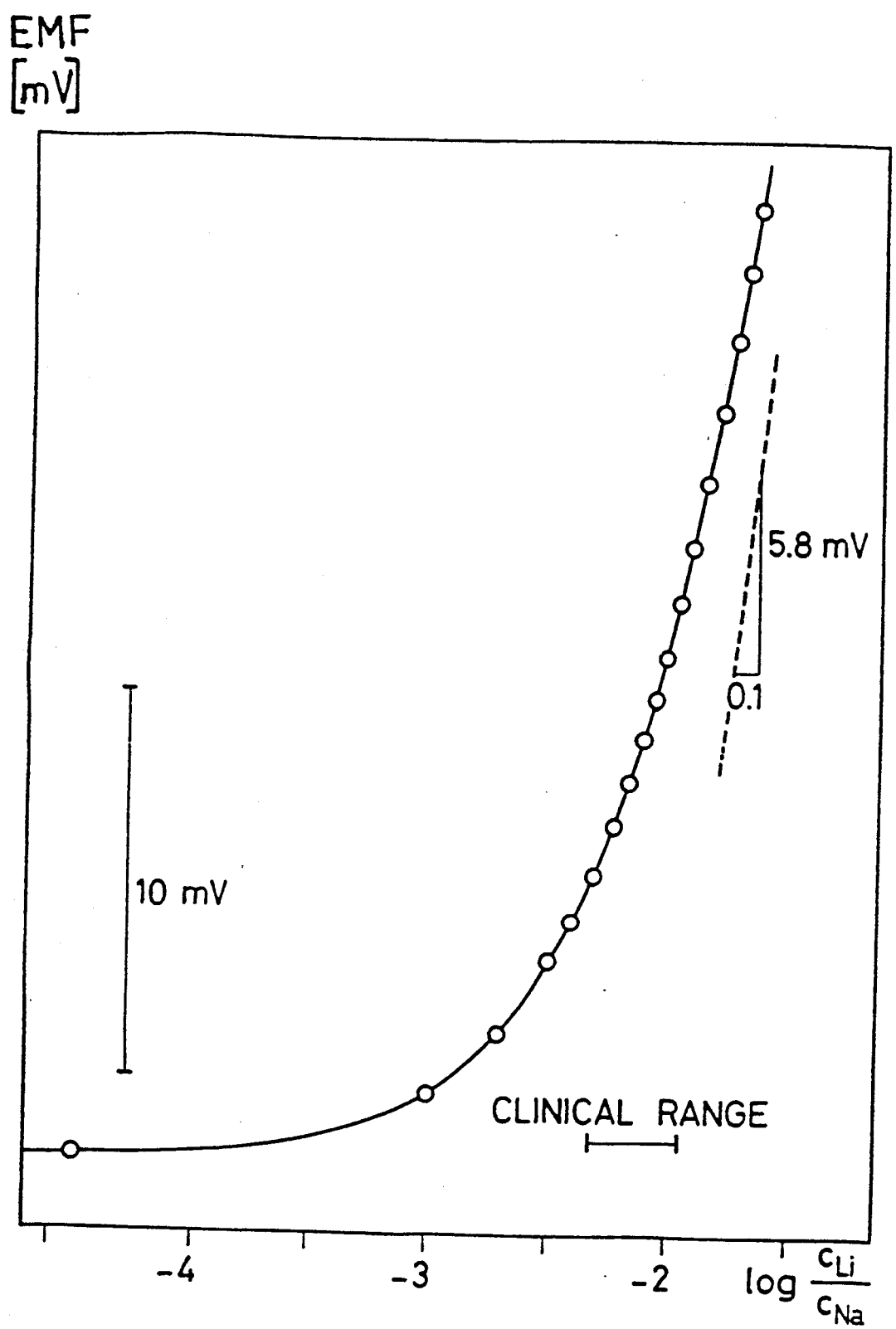
FIG. 2 is a calibration curve for determining the concentration ratio of lithium ions to sodium ions in a sample solution.

FIG. 2 illustrates the corresponding calibration curve.

On the ordinate of FIG. 2 there is plotted the EMF in mV, i.e. in millivolts. On the abscissa of said FIG. 2 there is plotted the value of $$\log \frac{c_{Li}}{c_{Na}}.$$

The concentration ratio of lithium ions to sodium ions was determined in a blood serum which had a sodium content of 145 mmol (see the corresponding value plotted near to the left end of the calibration curve of FIG. 2.

To said blood serum there were added small quantities of a solution which contained 50 mmol of lithium chloride per liter and furthermore 135 mmol of sodium chloride per liter.

It can be seen from the curve of FIG. 2 that the determined concentration ratios are in very good agreement with the above stated equation and accordingly also the response in samples of blood serum corresponds to said equation.

The curvature of the calibration curve corresponds to $$\log K_{LiNa}^{Pot} = -1.88.$$

The measurements the results of which are illustrated in FIG. 2 were performed using the lithium selective electrode which was equipped with the lithium selective membrane 3 according to example 1 and a sodium selective electrode which was equipped with the membrane 4 of example 1.

Furthermore said test showed that the residual standard deviation was extremely low, it was only 0.06 mV.

According to the inventive process therefore the concentration ratio of lithium ions to sodium ions could be determined in samples of undiluted serum with a far higher accuracy and a far better reproducibility than any prior art methods for the determination of lithium ions in serum. Accordingly said inventive process is also far superior to the assay of lithium ions until now performed in clinical laboratories, like the flame photometry or the atomic absorption spectrometry.

What is claimed is:

1. A process for the determination of the concentration ratio of lithium ions to sodium ions in a sample solution, in which higher concentrations of sodium ions are present than concentrations of lithium ions, which comprises the steps of:
   (a) contacting the sample solution with a lithium sensitive electrode which has a high selectivity for lithium ions over sodium ions in order to determine the presence of lithium ions;
   (b) contacting the sample solution with a sodium sensitive electrode which has a high selectivity for sodium ions over lithium ions in order to determine the presence of sodium ions;
   (c) determining the potential difference $\Delta V$ between the lithium sensitive electrode and the sodium sensitive electrode with a means for measuring said potential difference; and
   (d) calculating the concentration ratio of lithium ions to sodium ions based upon the potential difference $\Delta V$.

2. A process according to claim 1, wherein the means for measuring the potential difference between the sodium sensitive electrode and lithium sensitive electrode comprises a single external reference-electrode, wherein the potential difference $V_1$ between the lithium sensitive electrode and the reference-electrode and the potential difference $V_2$ between the sodium sensitive electrode and the reference-electrode is measured, and wherein the value $V_1 - V_2$ corresponds to the potential difference $\Delta V$ between the lithium sensitive electrode and sodium sensitive electrode.

3. A process according to claim 1, wherein the means for measuring the potential difference between the sodium sensitive electrode and lithium sensitive electrode comprises a common-electrode, wherein the potential difference $V_1$ between the lithium sensitive electrode and the common-electrode and the potential difference $V_2$ between the sodium sensitive electrode and the common-electrode is measured, and wherein the value $V_1 - V_2$ corresponds to the potential difference $\Delta V$ between the lithium sensitive electrode and sodium sensitive electrode.

4. A process according to claim 1, wherein the concentration ratio of lithium ions to sodium ions is determined in a sample of whole blood, blood serum or blood plasma where the lithium concentration is in the range of 0.7–1.5 mmol and the sodium concentration is in the range of 135–150 mmol.

* * * * *